United States Patent [19]

Langhauser et al.

[11] Patent Number: 5,831,106
[45] Date of Patent: Nov. 3, 1998

[54] PREPARATION OF BRIDGED METALLOCENE COMPLEXES

[75] Inventors: Franz Langhauser, Bad Dürkheim; David Fischer, Gönnheim; Günther Schweier, Friedelsheim, all of Germany; Hans-Herbert Brintzinger, Taegerswilen, Switzerland; Hans-Robert-Hellmuth Damrau, Constance, Germany

[73] Assignee: BASF Aktiengesellschaft, Ludwigshafen, Germany

[21] Appl. No.: 648,704

[22] Filed: May 16, 1996

[30] Foreign Application Priority Data

May 31, 1995 [DE] Germany ............ 195 19 884.0

[51] Int. Cl.$^6$ ............... C07F 7/08; C07F 3/02; C07F 7/28; C07F 7/30
[52] U.S. Cl. ............... 512/11; 556/1; 556/9; 556/12; 556/14; 556/19; 556/20; 556/21; 556/43; 556/53; 556/87; 556/95; 556/465; 556/413; 556/429; 556/428; 556/404; 260/665 R; 260/66 G; 549/206; 549/209; 549/210; 549/214
[58] Field of Search ............ 512/1, 9, 11, 12, 512/14, 19, 20, 21, 43, 53, 465, 87, 95, 413, 428, 427, 404; 260/665 R, 665 G; 549/206, 209, 210, 214

[56] References Cited

U.S. PATENT DOCUMENTS

| | | | |
|---|---|---|---|
| 5,103,030 | 4/1992 | Rohrmann et al. | 556/12 |
| 5,302,733 | 4/1994 | Diefenbach et al. | 556/11 |
| 5,359,105 | 10/1994 | Strickler et al. | 556/410 |
| 5,514,760 | 5/1996 | Karl et al. | 556/11 X |
| 5,543,373 | 8/1996 | Winter et al. | 556/12 X |
| 5,565,592 | 10/1996 | Patsidis et al. | 556/11 |

OTHER PUBLICATIONS

Wild et al., *J. of Org. Chem.*, 232, 1982, pp. 233–247.

*Primary Examiner*—Paul F. Shaver
*Attorney, Agent, or Firm*—Keil & Weinkauf

[57] ABSTRACT

A process for preparing metallocene complexes of the general

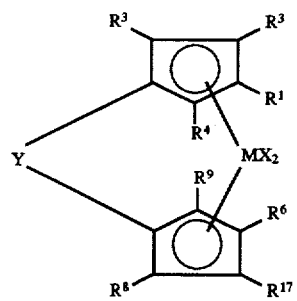

in which the substituents have the following meanings:

M is titanium, zirconium, hafnium, vanadium, niobium or tantalum,
X is fluorine, chlorine, bromine, iodine, hydrogen, $C_1$–$C_{10}$-alkyl, $C_6$–$C_{15}$-aryl or —$OR^5$,
where $R^5$ is $C_1$–$C_{10}$-alkyl, $C_6$–$C_{15}$-aryl, alkylaryl, arylalkyl, fluoroalkyl or fluoroaryl with, in each case, 1 to 10 carbon atoms in the alkyl radical and 6 to 20 carbon atoms in the aryl radical,
$R^1$ to $R^4$ and $R^6$ to $R^9$ are hydrogen, $C_1$–$C_{10}$-alkyl, 5- to 7-membered cycloalkyl which can in turn carry $C_1$–$C_{10}$-alkyls as substituents, or $C_6$–$C_{15}$-aryl or aryl-alkyl, it also being possible where appropriate for two adjacent radicals together to be cyclic groups having 4 to 15 carbon atoms, or $Si(R^{10})_3$ with
$R^{10}$ being $C_1$–$C_{10}$-alkyl, $C_6$–$C_{15}$-aryl or $C_3$–$C_{10}$-cycloalkyl,

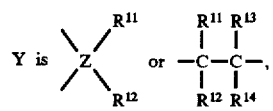

where Z is silicon, germanium, tin or carbon, and
$R^{11}$, $R^{12}$, $R^{13}$ and $R^{14}$ are hydrogen, $C_1$–$C_{10}$-alkyl, $C_3$–$C_{10}$-cycloalkyl or $C_6$–$C_{15}$-aryl, it also being possible where appropriate for two adjacent radicals together to be cyclic groups having 4 to 15 carbon atoms, which comprises reacting compounds of the general formula II
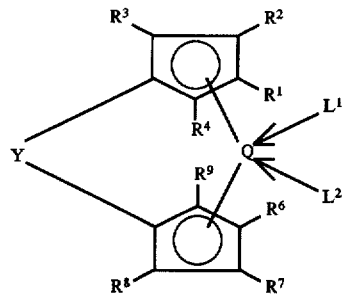
where
Q is beryllium, magnesium, calcium, strontium or barium, and
$L^1$ and $L^2$ are Lewis bases
with compounds of the general formula III
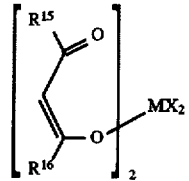
where
$R^{15}$ and $R^{16}$ are $C_1$–$C_{10}$-alkyl, $C_3$–$C_{10}$-cycloalkyl or $C_6$–$C_{15}$-aryl.
3 Claims, 1 Drawing Sheet

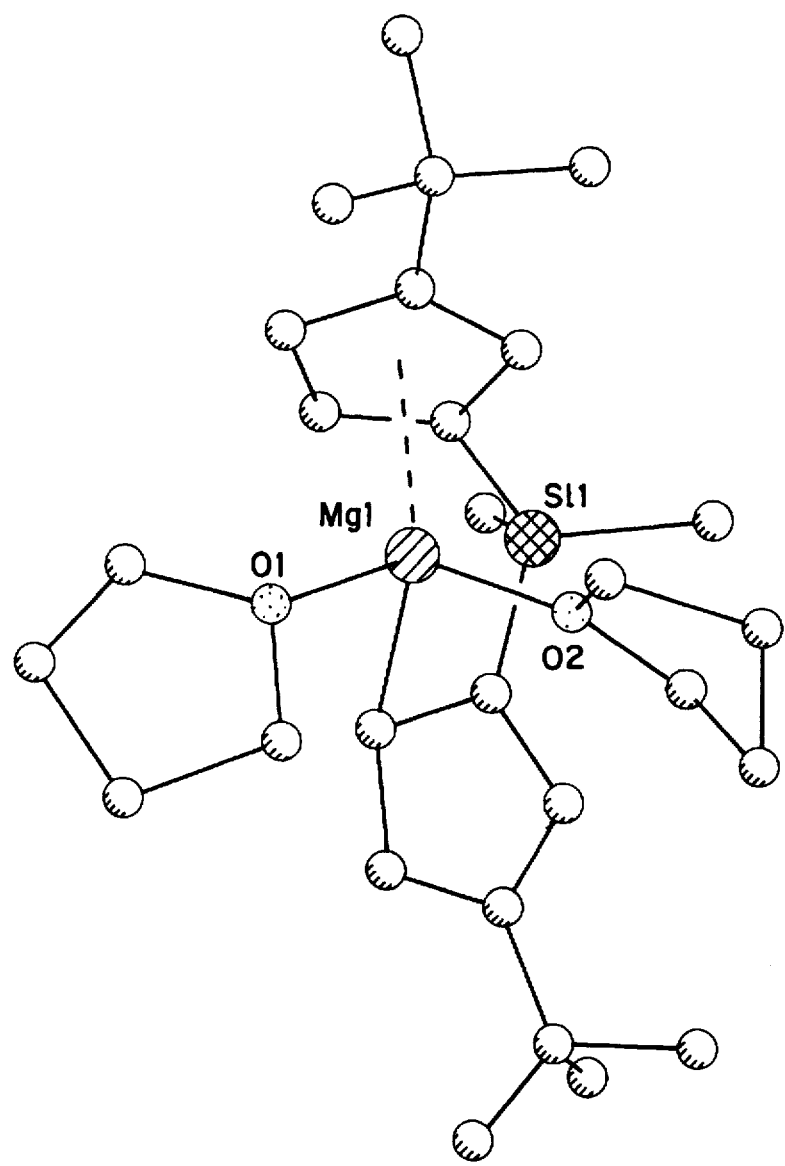

PREPARATION OF BRIDGED METALLOCENE COMPLEXES

The present invention relates to a process for preparing metallocene complexes of the general formula I

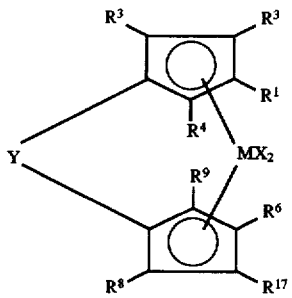

in which the substituents have the following meanings:

M is titanium, zirconium, hafnium, vanadium, niobium or tantalum,

X is fluorine, chlorine, bromine, iodine, hydrogen, $C_1$–$C_{10}$-alkyl, $C_6$–$C_{15}$-aryl or —$OR^5$, where $R^5$ is $C_1$–$C_{10}$-alkyl, $C_6$–$C_{15}$-aryl, alkylaryl, arylalkyl, fluoroalkyl or fluoroaryl with, in each case, 1 to 10 carbon atoms in the alkyl radical and 6 to 20 carbon atoms in the aryl radical, $R^1$ to $R^4$ and $R^6$ to $R^9$ are hydrogen, $C_1$–$C_{10}$-alkyl, 5- to 7-membered cycloalkyl which can in turn carry $C_1$–$C_{10}$-alkyls as substituents, or $C_6$–$C_{15}$-aryl or arylalkyl, it also being possible where appropriate for two adjacent radicals together to be cyclic groups having 4 to 15 carbon atoms, or $Si(R^{10})_3$ with $R^{10}$ being $C_1$–$C_{10}$-alkyl, $C_6$–$C_{15}$-aryl or $C_3$–$C_{10}$-cycloalkyl,

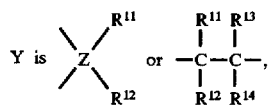

where Z is silicon, germanium, tin or carbon, and $R^{11}$, $R^{12}$, $R^{13}$ and $R^{14}$ are hydrogen, $C_1$–$C_{10}$-alkyl, $C_3$–$C_{10}$-cycloalkyl or $C_6$–$C_{15}$-aryl, it also being possible where appropriate for two adjacent radicals together to be cyclic groups having 4 to 15 carbon atoms.

BRIEF DESCRIPTION OF THE DRAWING

The figure is a structural representation of the bridged metallocene of the present application.

The present invention furthermore relates to compounds of the general formula II

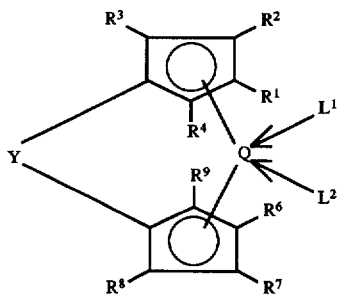

where

Q is beryllium, magnesium, calcium, strontium or barium, and $L^1$ and $L^2$ are Lewis bases, and to processes for preparing such compounds II and to the use of the compounds II for preparing the metallocene complexes I.

Bridged metallocene complexes are particularly suitable as catalysts in the preparation of polyolefins.

Metallocene complexes are normally prepared by reacting cyclopentadiene or substituted cyclopentadienes with organometallic reagents such as lithium alkyls or Grignard reagents or metal hydrides such as potassium hydride or alkali metals such as sodium. Reactions of these types are known and are described, for example, in F.R.W.P. Wild, L. Zsolnai, G. Huttner, H. H. Brintzinger, J. Organomet. Chem. 232 (1982) 233–247 or U.S. Pat. No. 5,359,105. The cyclopentadienyl-metal compounds obtained therefrom can be reacted, for example, with halides of group IVB of the Periodic Table to give the corresponding metallocene complexes which are bridged where appropriate. These reactions are also known and are described, for example, in EP-A 320 762 or U.S. Pat. No. 5,302,733.

The yields in the synthetic step in which the corresponding complex compound is prepared from a (bridged) biscyclopentadienyl dianion are, in particular, normally poor or unsatisfactory. Furthermore, the reagents for the preparation are, in some cases, costly (methyllithium) and objectionable from the viewpoint of safety (potassium hydride). When lithium alkyls are used, reaction with the transition metal chlorides results in lithium chloride which is very difficult to remove and often remains in the product as impurity.

It is an object of the present invention to find a way of synthesizing metallocene complexes which both provides satisfactory yields and represents a distinct improvement from the viewpoint of safety and from that of cost.

We have found that this object is achieved by a process for preparing metallocene complexes of the general formula I, wherein compounds of the general formula II

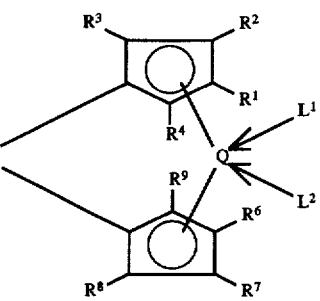

where

Q is beryllium, magnesium, calcium, strontium or barium, and $L^1$ and $L^2$ are Lewis bases, are reacted with compounds of the general formula III

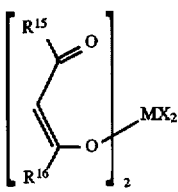

where

R$^{15}$ and R$^{16}$ are C$_1$–C$_{10}$-alkyl, C$_3$–C$_{10}$-cycloalkyl or C$_6$–C$_{15}$-aryl.

We have also found compounds of the general formula II, and processes for preparing such compounds II and the use of the compounds II for preparing the metallocene complexes I.

The process according to the invention is preferably used to prepare metallocene complexes of the general formula I where M is titanium, zirconium or hafnium,
X is chlorine or methyl,
R$^1$ to R$^4$ and R$^6$ to R$^9$ are hydrogen, C$_1$–C$_{10}$-alkyl or where two adjacent radicals together are cyclic groups having 4 to 15 carbon atoms, in particular 8 to 12 carbon atoms,
Z is silicon or carbon, and
R$^{11}$, R$^{12}$, R$^{13}$ and R$^{14}$ are hydrogen or C$_1$–C$_4$-alkyl.

Examples of particularly preferred metallocene complexes I include
dimethylsilanediylbis(cyclopentadienyl)zirconium dichloride,
dimethylsilanediylbis(indenyl)zirconium dichloride,
dimethylsilanediylbis(tetrahydroindenyl)zirconium dichloride,
ethylenebis(cyclopentadienyl)zirconium dichloride,
ethylenebis(indenyl)zirconium dichloride,
ethylenebis(tetrahydroindenyl)zirconium dichloride,
ethylenebis(2-methylindenyl)zirconium dichloride,
ethylenebis(2-methylindenyl)hafnium dichloride,
ethylenebis(2-methylbenzindenyl)zirconium dichloride,
ethylenebis(2-methylbenzindenyl)hafnium dichloride,
dimethylsilanediylbis(3-tert-butyl-5-methylcyclopentadienyl)-zirconium dichloride,
dimethylsilanediylbis(3-tert-butyl-5-ethylcyclopentadienyl)-zirconium dichloride,
dimethylsilanediylbis(3-tert-butyl-5-methylcyclopentadienyl)-dimethylzirconium,
dimethylsilanediylbis(2-methylindenyl)zirconium dichloride,
dimethylsilanediylbis(2-isopropylindenyl)zirconium dichloride,
dimethylsilanediylbis(2-tert-butylindenyl)zirconium dichloride,
diethylsilanediylbis(2-methylindenyl)zirconium dibromide,
dimethylsilanediylbis(2,5-dimethylcyclopentadienyl)zirconium dichloride,
dimethylsilanediylbis(2-ethyl-5-isopropylcyclopentadienyl)-zirconium dichloride,
dimethylsilanediylbis(2-methylbenzindenyl)zirconium dichloride,
dimethylsilanediylbis(2-methylindenyl)hafnium dichloride and
isopropylidenecyclopentadienylfluorenylzirconium dichloride.

In the process according to the invention, compounds of the general formula II

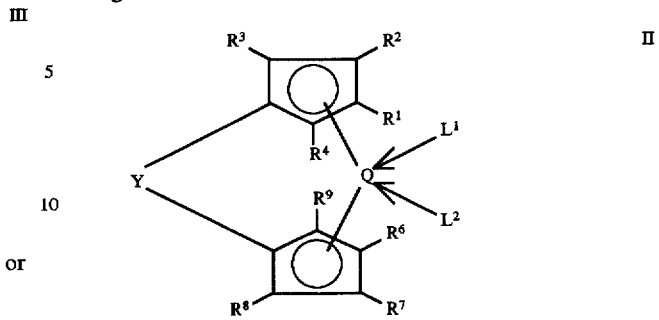

are reacted with compounds of the general formula III

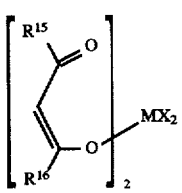

Preferred compounds of the general formula II are those where

Q is magnesium, and the radicals R$^1$ to R$^4$ and R$^6$ to R$^9$ and Y have the preferred meanings stated for the metallocene complexes I.

Suitable Lewis bases L$^1$ and L$^2$ are, in principle, all neutral nucleophilic reagents, for example amines, phosphines, ethers and sulfides; the Lewis bases can be mono-, bi- or polyfunctional. L$^1$ and L$^2$ are particularly preferably the same and are linear or, in particular, cyclic ethers, preferably tetrahydrofuran (THF).

Preferred compounds of the general formula III are those where

R$^{15}$ and R$^{16}$ are C$_1$–C$_6$-alkyl, and the R$^{15}$ and R$^{16}$ radicals are, in particular, the same and are methyl.

Concerning the preferred meanings of M and X, reference may be made to what has been said about the metallocene complexes I.

A very particularly preferred compound of the formula III is bis(acetylacetonato)zirconium dichloride.

Compounds of the general formula III and processes for their preparation are known and are described, for example, in T. J. Pinnavia et al., Inorg. Chem. 7(3) (1968) 502–508.

Compounds II can be reacted with compounds III at temperatures in the range from −80° C. to +160° C., preferably from 0° C. to 120° C., preferably in an organic solvent, for preference in aromatic hydrocarbons such as toluene or ethylbenzene. The reaction time can be from 1 to 48 hours. It has proven particularly suitable for the molar ratio of II to III to be in the range from 0.8:1 to 1.2:1.

The workup of the resulting metallocene complex I is not critical and can take place, for example, by filtration, where appropriate with the assistance of a filtration aid such as kieselguhr.

Compounds of the general formula II are novel and can be prepared, for example, by the following process:

Compounds of the general formula IV

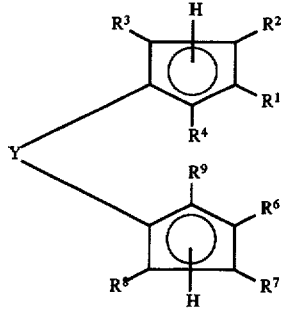

can be reacted with compounds of the general formula V

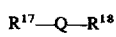

and with Lewis bases $L^1$ and $L^2$.

Concerning the preferred meanings of the radicals $R^1$ to $R^4$ and $R^6$ to $R^9$, and Y, Q and of the Lewis bases $L^1$ and $L^2$, reference may be made to what has already been said.

The radicals $R^{17}$ and $R^{18}$ in the general formula V are hydrogen, $C_1$–$C_{10}$-alkyl, $C_3$–$C_{10}$-cycloalkyl, $C_6$–$C_{15}$-aryl, alkylaryl or aryl-alkyl with, in each case, 1 to 10 carbon atoms in the alkyl radical and 6 to 20 carbon atoms in the aryl radical. $R^{17}$ and $R^{18}$ are preferably the same and are $C_1$–$C_6$-alkyl.

Compounds of the formula IV can be reacted with compounds of the formula V in organic solvents such as aliphatic or aromatic hydrocarbons, for example heptane or petroleum ether, and the temperatures can be in the range from $-80°$ C. to $+160°$ C., preferably from $20°$ C. to $120°$ C. The reaction time can be from 1 to 48 hours. It has proven particularly suitable for the molar ratio of IV to V to be in the range from 0.8:1 to 1.2:1. The Lewis bases $L^1$ and $L^2$ are then added, preferably at temperatures in the range from $-10°$ to $+100°$ C. The molar ratio of $L^1$ and $L^2$ to V is preferably from 2:1 to 40:1, and the molar ratio of $L^1$ and $L^2$ to IV is preferably in the range from 2:1 to 40:1. The resulting compound II can then be filtered off and dried.

Compounds of the general formula IV and processes for their preparation are known and are described, for example, in W. A. Hermann et al., Angew. Chemie 101 (1989) 1536–1538, and W. Spaleck et al., New J. Chem. 14 (1990) 499–503.

The compounds II are suitable for preparing metallocene complexes of the general formula I. The process according to the invention for preparing metallocene complexes I is distinguished by high yields, low safety risk and low costs.

EXAMPLES

Example 1

Preparation of dimethylsilanediylbis(3-tert-butylcyclopenta-dienyl)zirconium dichloride I1

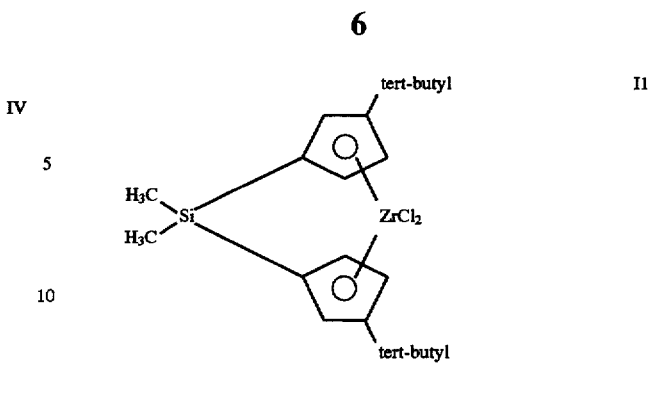

Example 1a

Preparation of dimethylsilanediylbis(3-tert-butylcyclopenta-dienyl)magnesium * 2THF II1

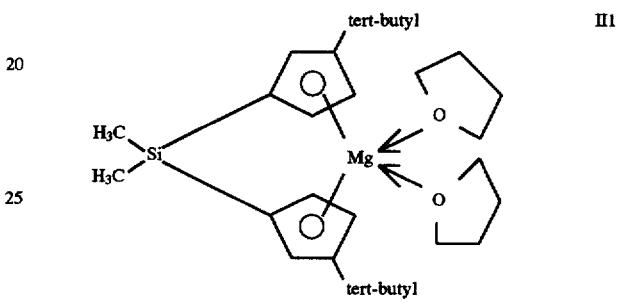

10.5 ml (10.5 mmol) of a 1 molar solution of dibutylmagnesium (V1) in heptane were added to 200 ml of absolute heptane. To this were added over the course of 15 minutes, while stirring at room temperature, 3.14 g (10.5 mmol) of dimethyl-silanediylbis(3-tert-butylcyclopentadiene) (IV1), dissolved in 30 ml of heptane.

The reaction solution was then heated to boiling. After 12 hours under reflux, the mixture was concentrated to half the amount of solvent, and 1.8 ml (22 mmol) of tetrahydrofuran were added. The resulting reaction mixture was cooled to $-30°$ C. for 12 h. The white precipitate was then filtered off in the cold under inert gas through a sintered glass filter and dried at room temperature and 0.1 mbar for 2 h. 4 g (8.6 mmol, 82%) of the magnesocene II1 were obtained (cf. FIG. 1: Crystal structure of II1).

$^1$H-NMR spectrum, internal standard $C_6D_6$ (7.15 ppm), 250 MHz

| Chem. shift | Mult. | Assignment |
|---|---|---|
| 6.59–6.18 | m | —$C_5H_3$ |
| 6.18–5.6 | b | |
| 3.75 | m, 8 | THF |
| 1.85 | m, 8 | THF |
| 1.50–1.30 | m | —$C(CH_3)_3$ |
| 1.30–1.10 | b | |
| 0.42 | b | —$Si(CH_3)_2$ |
| 0.30–0.15 | m | |

Example 1b

Preparation of I1

0.76 g (2.12 mmol) of bis(acetylacetonato)zirconium dichloride (III1) was dissolved in 100 ml of toluene. To this was added, while stirring at room temperature, 1.00 g (2.12 mmol) of the magnesocene II1 dissolved in 40 ml of toluene. The mixture was then heated at $80°$ C. for 8 hours.

After cooling to room temperature, the resulting precipitate was filtered through a sintered disk charged with baked kieselguhr, and the filtrate was completely freed of solvent. The filtrate as then taken up in 50 ml of pentane, again filtered and cooled to −80° C. After 24 h, the precipitated product was filtered off and dried at room temperature and 0.1 mbar for 2 h. 0.78 g (1.70 mmol, 80%) of compound I1 was obtained.

$^1$H-NMR spectrum, internal standard $CDCl_3$ (7.26 ppm), 250 MHz

| rac | meso | Assignment |
|---|---|---|
| 0.19 (s, 6) | 0.08 (s, 3) | —Si(CH$_3$)$_2$ |
|  | 0.29 (s, 3) |  |
| 1.39 (s, 18) | 1.45 (s, 18) | —C(CH$_3$)$_3$ |
| 5.67 (m, 4) | 5.54 (pt, 2) | Cp-H |
|  | 5.87 (pt, 2) |  |
| 6.72 (pt, 2) | 6.84 (pt, 2) | Cp-H | pt = pseudotriplet

Example 2

Preparation of dimethylsilanediylbis(2-methylbenzindenyl)-zirconium dichloride I2

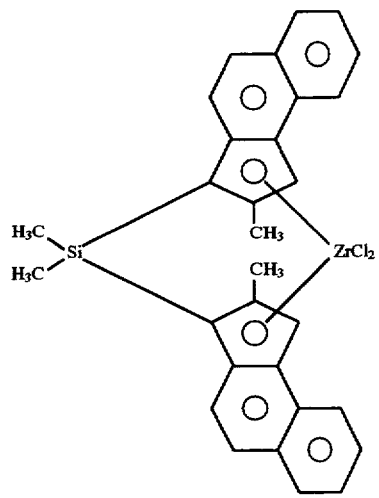

Example 2a

Preparation of dimethylsilanediylbis(2-methylbenzindenyl)-magnesium * 2THF II2

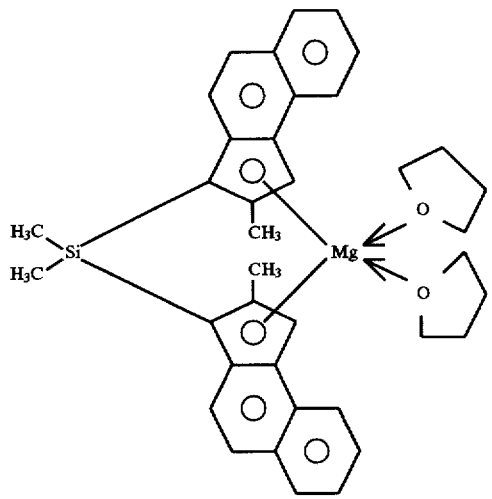

The procedure was as in Example 1a but 9.2 ml (9.2 mmol) of a 1 molar solution of dibutylmagnesium (V1) in heptane and 3.83 g (9.2 mmol) of dimethylsilanediylbis(2-methylbenzindene) (IV2), dissolved in 50 ml of heptane, were used. 4.6 g (7.8 mmol, 85%) of the magnesocene II2 were obtained.

$^1$H-NMR spectrum, internal standard $C_6D_6$ (7.15 ppm), 250 MHz

| Chem. shift | Mult. | Assignment |
|---|---|---|
| 6.20–8.50 | m, 14 |  |
| 2.95 | m, 8 | THF |
| 0.85 | m, 8 | THF |
| 1.70 | sb | Cp-CH$_3$ |
| 2.45 | sb |  |
| 0.30/0.25/0.18 | sb | —Si(CH$_3$)$_2$ | sb = singlet, broad

Example 2b

Preparation of I2

0.185 g (0.51 mmol) of bis(acetylacetonato)zirconium dichloride (III1) was dissolved in 60 ml of toluene. To this was added, while stirring at room temperature, 0.3 g (0.51 mmol) of the magnesocene II2 dissolved in 20 ml of toluene. The mixture was then heated at 80° C. for 8 hours. After cooling to room temperature, the solvent was completely removed under oil pump vacuum, and the residue was extracted with 100 ml of toluene for 8 hours. Renewed removal of the solvent under oil pump vacuum resulted in 0.26 g (0.45 mmol, 89%) of compound I2.

$^1$H-NMR spectrum, internal standard $CDCl_3$ (7.26 ppm), 250 MHz

| Chem. shift | Mult. | Assignment |
|---|---|---|
| 1.34 | s, 6 | —Si(CH$_3$)$_2$ |
| 2.35 | s, 6 | Cp-CH$_3$ |
| 7.14–7.96 | m, 14 |  |

Comparative Example C1

Preparation of I2

7.0 g (16.7 mmol) of dimethylsilanediylbis(2-methylbenzindene) dissolved in 120 ml of THF were added to a suspension of 2.8 g (70 mmol) of potassium hydride in 50 ml of THF at room temperature. The mixture was then stirred at room temperature for 8 hours. The supernatant solution was added to a solution of 3.9 g (16.7 mmol) of $ZrCl_4$ in 80 ml of THF. This mixture was stirred at room temperature for 72 hours and then filtered, and the solvent was subsequently completely removed under 0.1 mbar, and the resulting residue was mixed with 140 ml of toluene and stirred for 12 hours. The remaining microcrystalline precipitate was filtered off and washed successively with 15 ml of toluene, 20 ml of THF and 10 ml of methylene chloride. It was then dried at room temperature and 0.1 mbar for 4 hours. 3.4 g (5.8 mmol, 35%) of compound I2 were obtained.

We claim:

1. A process for preparing metallocene complexes of the general formula I

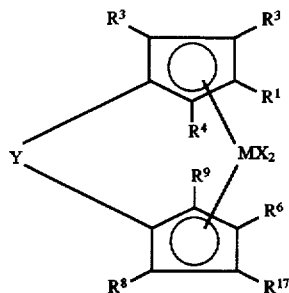

in which the substituents have the following meanings:

M is titanium, zirconium, hafnium, vanadium, niobium or tantalum,

X is fluorine, chlorine, bromine, iodine, hydrogen, $C_1$–$C_{10}$-alkyl, $C_6$–$C_{15}$-aryl or —$OR^5$, where $R^5$ is $C_1$–$C_{10}$-alkyl, $C_6$–$C_{15}$-aryl, alkylaryl, arylalkyl, fluoroalkyl or fluoroaryl with, in each case, 1 to 10 carbon atoms in the alkyl radical and 6 to 20 carbon atoms in the aryl radical, $R^1$ to $R^4$ and $R^6$ to $R^9$ are hydrogen, $C_1$–$C_{10}$-alkyl, 5- to 7-membered cycloalkyl which can in turn carry $C_1$–$C_{10}$-alkyls as substituents, or $C_6$–$C_{15}$-aryl or arylalkyl, it also being possible where appropriate for two adjacent radicals together to be cyclic groups having 4 to 15 carbon atoms, or $Si(R^{10})_3$ with $R^{10}$ being $C_1$–$C_{10}$-alkyl, $C_6$–$C_{15}$-aryl or $C_3$–$C_{10}$-cycloalkyl,

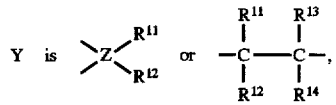

where Z is silicon, germanium, tin or carbon, and $R^{11}, R^{12}, R^{13}$ and $R^{14}$ are hydrogen, $C_1$–$C_{10}$-alkyl, $C_3$–$C_{10}$-cycloalkyl or $C_6$–$C_{15}$-aryl, it also being possible where appropriate for two adjacent radicals together to be cyclic groups having 4 to 15 carbon atoms, which comprises reacting compounds of the general formula II

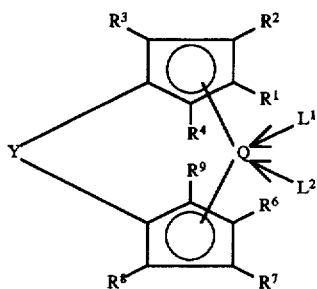

where

Q is beryllium, magnesium, calcium, strontium or barium, and $L^1$ and $L^2$ are Lewis bases with compounds of the general formula III

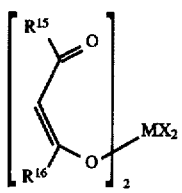

where $R^{15}$ and $R^{16}$ are $C_1$–$C_{10}$-alkyl, $C_3$–$C_{10}$-cycloalkyl or $C_6$–$C_{15}$-aryl.

2. A compound of the formula II

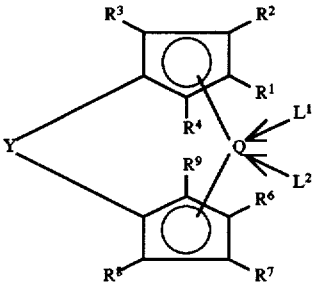

in which the substituents have the following meanings:

$R^1$ to $R^4$ and $R^6$ to $R^9$ are hydrogen, $C_1$–$C_{10}$-alkyl, 5- to 7-membered cycloalkyl which can in turn carry $C_1$–$C_{10}$-alkyls as substituents, or $C_6$–$C_{15}$-aryl or arylalkyl, it also being possible where appropriate for two adjacent radicals together to be cyclic groups having 4 to 15 carbon atoms, or $Si(R^{10})_3$ with $R^{10}$ being $C_1$–$C_{10}$-alkyl, $C_6$–$C_{15}$-aryl or $C_3$–$C_{10}$-cycloalkyl,

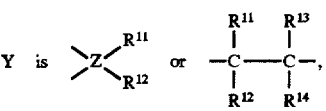

where Z is silicon, germanium, tin or carbon, and $R_{11}, R^{12}, R^{13}$ and $R^{14}$ are hydrogen, $C_1$–$C_{10}$-alkyl, $C_3$–$C_{10}$-cycloalkyl or $C_6$–$C_{15}$-aryl, it also being possible where appropriate for two adjacent radicals together to be cyclic groups having 4 to 15 carbon atoms, Q is beryllium, magnesium, calcium, strontium or barium, and $L^1$ and $L^2$ are Lewis bases.

3. A process for preparing compounds of the general formula II as claimed in claim 2, which comprises reacting compounds of the general formula IV

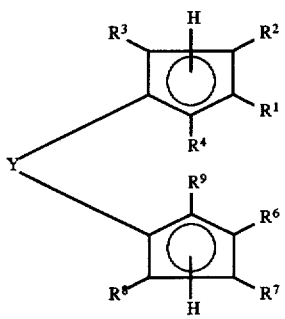

IV with compounds of the general formula V

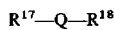

V where

R$^{17}$ and R$^{18}$ are hydrogen, C$_1$–C$_{10}$-alkyl, C$_3$–C$_{10}$-cycloalkyl, C$_6$–C$_{15}$-aryl, alkylaryl or arylalkyl with, in each case, 1 to 10 carbon atoms in the alkyl radical and 6 to 20 carbon atoms in the aryl radical, and with Lewis bases L$^1$ and L$^2$.

* * * * *

UNITED STATES PATENT AND TRADEMARK OFFICE
CERTIFICATE OF CORRECTION

PATENT NO.: 5,831,106

DATED: November 3, 1998

INVENTOR(S): LANGHAUSER et al.

It is certified that error appears in the above-identified patent and that said Letters Patent is hereby corrected as shown below:

In the abstract, item [57], line 1, after "general" insert --formula I--.

In the abstract, item [57], in formula I, "$R^{17}$" should be --$R^7$--.

In the abstract, item [57], line 12 after formula I, "aryl-alkyl" should be --arylalkyl--.

Col. 9, claim 1, line 33, "$R^{17}$" should be --$R^7$--.

Signed and Sealed this

Sixteenth Day of February, 1999

Attest:

Attesting Officer

*Acting Commissioner of Patents and Trademarks*